(12) United States Patent
Myhren et al.

(10) Patent No.: US 8,349,834 B2
(45) Date of Patent: Jan. 8, 2013

(54) DIOXOLANE DERIVATES FOR THE TREATMENT OF CANCER

(75) Inventors: Finn Myhren, Porsgunn (NO); Marit Liland Sandvold, Porsgrunn (NO); Steinar Hagen, Hagan (NO); Ole Henrik Eriksen, Oslo (NO)

(73) Assignee: Clavis Pharma AS, Oslo (NO)

( * ) Notice: Subject to any disclaimer, the term of this patent is extended or adjusted under 35 U.S.C. 154(b) by 714 days.

(21) Appl. No.: 12/305,338

(22) PCT Filed: Dec. 7, 2006

(86) PCT No.: PCT/NO2006/000469
§ 371 (c)(1),
(2), (4) Date: Aug. 26, 2009

(87) PCT Pub. No.: WO2007/067071
PCT Pub. Date: Jun. 14, 2007

(65) Prior Publication Data
US 2010/0062996 A1 Mar. 11, 2010

(30) Foreign Application Priority Data
Dec. 8, 2005 (NO) .................................. 20055841

(51) Int. Cl.
*A01N 43/64* (2006.01)
*A01N 43/66* (2006.01)
*A61K 31/53* (2006.01)
*C07F 9/02* (2006.01)
*C07D 473/00* (2006.01)

(52) U.S. Cl. ........ 514/241; 514/242; 514/243; 514/244; 514/245; 544/243; 544/264

(58) Field of Classification Search .................. None
See application file for complete search history.

(56) References Cited

U.S. PATENT DOCUMENTS

| | | | |
|---|---|---|---|
| 5,223,263 A | 6/1993 | Hostetler et al. | 424/450 |
| 5,270,315 A | 12/1993 | Belleau et al. | 514/262 |
| 5,817,667 A | 10/1998 | Chu et al. | 514/274 |
| 6,153,594 A | 11/2000 | Børretzen et al. | 514/43 |
| 6,316,425 B1 | 11/2001 | Myhren et al. | 514/49 |
| 6,335,322 B1 * | 1/2002 | Myhren et al. | 514/49 |
| 6,372,725 B1 | 4/2002 | Zilch et al. | 514/48 |
| 6,384,019 B1 | 5/2002 | Myhren et al. | 514/49 |
| 6,525,033 B1 | 2/2003 | Schinazi et al. | 514/47 |
| 6,548,486 B1 | 4/2003 | Dalen et al. | 514/43 |
| 6,566,365 B1 | 5/2003 | Storer | 514/261 |
| 6,576,636 B2 | 6/2003 | Webb et al. | 514/261 |
| 6,670,341 B1 | 12/2003 | Kucera et al. | 514/77 |
| 2003/0013660 A1 | 1/2003 | Attardo et al. | 514/18 |

FOREIGN PATENT DOCUMENTS

| | | |
|---|---|---|
| CA | 2468099 | 5/2003 |
| EP | 0056265 | 7/1982 |
| EP | 0393920 | 10/1990 |
| EP | 1468687 | 10/2004 |
| WO | WO 92/03462 | 3/1992 |
| WO | WO 94/09793 A1 | 5/1994 |
| WO | WO 98/32718 | 7/1998 |
| WO | WO 99/26958 | 6/1999 |
| WO | WO 01/18013 | 3/2001 |

OTHER PUBLICATIONS

Jennings, R. et al., "Evaluation of a Novel, Anti-Herpes Simplex Virus Compound, Acyclovir Elaidate (P-4010), in the Female Guinea Pig Model of Genital Herpes," Antimicrobial Agents & Chemotherapy, 43(1):53-61 (1999).

Andrei, G. et al., "Antiviral activity of ganciclovir elaidic acid ester against herpesviruses," Antiviral Research, 45:157-167 (2000).

Balzarini, J. et al., "Brief Communication: Superior cytostatic activity of the ganciclovir elaidic acid ester due to the prolonged intracellular retention of ganciclovir anabolites in herpes simplex virus type 1 thymidine kinase gene-transfected tumor cells," Gene Therapy, 5:419-426 (1998).

Breistøl, K. et al., "Antitumor Activity of P-4055 (Elaidic Acid-Cytarabine) Compared to Cytarabine in Metastatic and s.c. Human Tumor Xenograft Models," Cancer Research, 59:2944-2949 (1999).

Bergman, A.M. et al., "Antiproliferative activity and mechanism of action of fatty acid derivatives of arabinofuranosylcytosine in leukemia and solid tumor cell lines," Biochemical Pharmacology, 67:503-511 (2004).

Cecil Textbook of Medicine, edited by Bennet, J.C., and Plum F., 20$^{th}$ Edition, 1:1004-1010 (1996).

Lambert, D.M., "Rationale and applications of lipids as prodrug carriers," European Journal of Pharmaceutical Sciences, 11 (Suppl. 2):S15-S27 (2000).

Wood et al., "Past and Future of the Mitotic Spindle as an Oncology Target," Current Opinion in Pharmacology, 1:370-377 (2001).

(Continued)

*Primary Examiner* — Lawrence E Crane

(74) *Attorney, Agent, or Firm* — Fitzpatrick, Cella, Harper & Scinto

(57) ABSTRACT

This invention relates to certain unsaturated fatty acid derivatives of therapeutically active 1,3-dioxolane nucleoside analogues and to pharmaceutical formulations containing them. The said derivatives fall within formula (I). Compounds of formula (I) can be used in the treatment of a cancerous disease, including solid tumors and haematological cancers such as leukaemias, lymphomas and multiple myelomas.

(I)

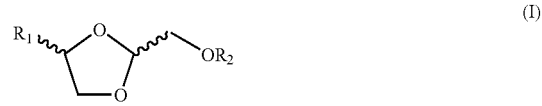

7 Claims, No Drawings

OTHER PUBLICATIONS

Cheng, Y.C., "Potential use of antiviral L(−)nucleoside analogues for the prevention or treatment of viral associated cancers," Cancer Letters, 162 (Suppl. 1):S33-S37 (2001).

Office Action issued in Australian Patent Application No. 2006-323278 (May 17, 2011) (3 pages).

Wilson, L.J., et al., "The Synthesis and Anti-HIV Activity of Pyrimidine Dioxolanyl Nucleosides," Bioorganic & Medical Chemistry Letters, vol. 3, No. 2, pp. 169-174 (1993).

US 2001/0020026 A1, 09/2001, Belleau et al. (withdrawn)

* cited by examiner

DIOXOLANE DERIVATES FOR THE TREATMENT OF CANCER

This application is a 35 U.S.C. §371 of International Application No. PCT/NO2006/000469, filed Dec. 7, 2006, which claims the benefit of Norwegian patent application no. 20055841, filed Dec. 8, 2005, all of which are incorporated by reference herein.

FIELD OF INVENTION

This invention relates to certain unsaturated fatty acid derivatives of therapeutically active 1,3-dioxolane nucleoside analogues and to pharmaceutical formulations containing them. The said derivatives are referred to as "Compounds of formula I" herein. Compounds of formula I can be used in the treatment of a cancerous disease. Treatment of both solid tumours and haematological cancers such as leukaemias, lymphomas and multiple myelomas are included.

TECHNICAL BACKGROUND

Nucleoside analogues, the derivatives of the natural nucleosides found as building blocks of DNA and RNA, are effective in the clinical treatment of human cancer or viral diseases, although in the early years such compounds were evaluated as anti-tuberculosis agents. Such compounds have been registered in the market for more than 40 years, and approximately 35 products are currently in daily use. The natural nucleosides illustrated in the FIGURE below, are constructed from two classes of nitrogen bases, the purines exemplified by adenine and guanine and the pyrimidines exemplified by thymine, uracil and cytosine, and from the monosaccharide ribose or deoxyribose.

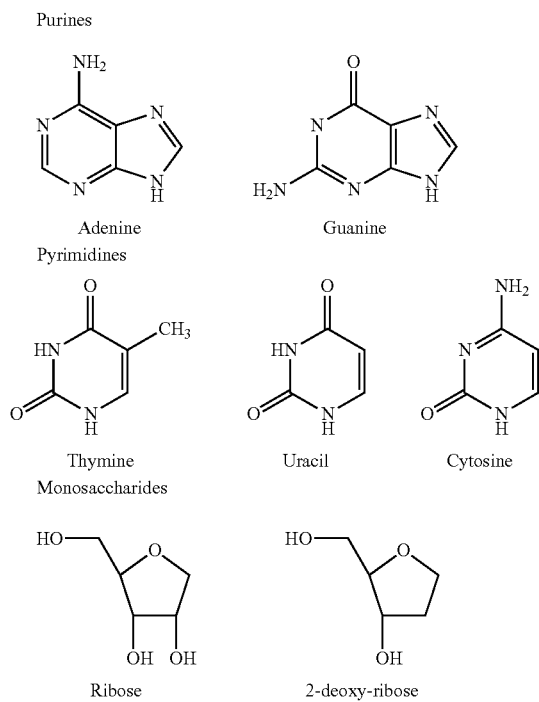

The natural nucleosides all exist in the so called β-D configuration as illustrated in the formula A, below. The nitrogen base and the hydroxy-methyl side chain on the sugar ring are both on the same side (cis) of the plane of the sugar ring.

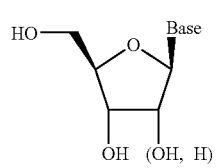

Formula A

If the two groups are on either side (trans), it is referred to as the α isomer.

In order to obtain nucleoside derivatives with anticancer or antiviral activity, chemical modifications in either the nitrogen base and/or the monosaccharide have been performed. For instance the addition of halogen atoms, the substitution of OH groups with other functional groups or a stereochemical change from ribose to arabinose may lead to products with a potential therapeutic benefit. In many products, the monosaccharide ring is conserved, while in others, the sugar ring has been changed into a chain. The nucleoside analogues are small molecules with fair to excellent aqueous solubility.

The extensive research and development effort put into the area of nucleoside analogues due to the worldwide AIDS epidemic bolstered the basic knowledge and understanding of mechanism of action, alterations in activity profile due to chemical modifications etc, also relevant to the field of cancer treatment.

A general weakness with many drugs, including nucleoside analogues, is low activity and inferior specificity for treatment of the actual disease in question. Some of these problems may be related to the inherent activity of the drug substance itself, some may be related to certain resistance mechanisms (either inherent in the patient or acquired during treatment e.g. MDR in cancer treatment). Some problems may be related to certain inferior transport or cellular uptake and activation mechanisms. Some problems may be related to rapid inactivation and/or excretion of the drug.

The efficacy of nucleoside analogues depends on a large extent on their ability to mimic natural nucleosides, thus interacting with viral and/or cellular enzymes and interfering with or inhibiting critical processes in the metabolism of nucleic acids. In order to exert their antiviral or anti cancer activity, the nucleoside analogues have to be transformed, via their mono- and di-phosphates, into their corresponding tri-phosphates through the action of viral and/or cellular kinases. As a general rule, the tri-phosphate is the active agent, but for some products, e.g. gemcitabine, even the di-phosphate may exert a clinically significant effect.

In order to reach the diseased, cancerous or virus infected cells or tissues, following either enteral or parenteral administration, the nucleoside analogues should have favourable pharmacokinetic characteristics. In addition to rapid excretion of the administered drug, many nucleoside analogues may be deactivated both in the blood stream and in tissues. For instance may cytosine derivatives, even at the monophosphate level, be rapidly deaminated through the action of a class of enzymes called deaminases, to the inactive uracil analogue. The cellular uptake and thus good therapeutic efficacy of many nucleoside analogues strongly depend on membrane bound nucleoside transport proteins (called concentrative and equilibrative nucleoside transporters). Hence compounds that do not rely on such specific uptake mechanisms are sought for. Yet another activity limiting factor, particularly within the anti cancer field, are the cellular repair mechanisms. When an anti-cancer nucleoside analogue mono-phosphate is incorporated into the cellular DNA, it should not be removed from the cancer cell DNA due to the exonuclease activity linked to the p53 protein. However, removal of a nucleoside analogue from the DNA of a healthy cell is favourable in order to limit the side effects of the drug.

Over the years, many nucleoside analogues have been developed that to a large extent overcome some or many of the activity limiting features. As an example, acyclovir (ACV) can be given to illustrate a compound with great specificity. The ACV-mono-phosphate can only be formed by viral kinases meaning that ACV cannot be activated in uninfected cells. Despite this fact, ACV is not a particularly active product. In order to circumvent the often rate limiting step in the activation of a nucleoside analogue, the intracellular formation of the nucleoside analogue mono-phosphate, several phosphonate such as cidofovir or even mono-phosphate products, have been developed. In order to facilitate oral uptake or to secure a favourable drug disposition in the body, particular prodrugs such as Hepsera have been made.

In addition to the structural changes made to nucleoside analogues to facilitate enhanced clinical utility, further modifications have been made to improve the activity. The Applicant of the present invention (U.S. Pat. No. 6,153,594, U.S. Pat. No. 6,548,486 B1, U.S. Pat. No. 6,316,425 B1, U.S. Pat. No. 6,384,019 B1) and several other groups have modified nucleoside analogues through the addition of lipid moieties (EP-A-56265, EP-A-393920, WO 99/26958). This can be achieved by the linking of fatty acids through for instance an ester, amide, carbonate or carbamate bond. More elaborate products can be made, such as phospholipid derivatives (Eur J Pharm Sci (2000) 11b Suppl 2: p 15-27, EP 545966 B1, CA 2468099 A1, U.S. Pat. No. 6,372,725 B1 and U.S. Pat. No. 6,670,341 B1) of the nucleoside analogues. Such analogues are described to have antiviral activity that is particularly suitable for the therapy and prophylaxis of infections caused by DNA, RNA or retroviruses. They are also suited for treatment of malignant tumours. The nucleoside analogue lipid derivatives may serve several purposes. They may be regarded as a prodrug that is not a substrate for deaminases, thereby protecting the nucleoside analogues from deactivation during transport in the bloodstream. The lipid derivatives may also be more efficiently transported across the cellular membrane resulting in enhanced intracellular concentration of the nucleoside analogue. Lipid derivatives may also be more suited for use in dermal preparations, oral products (U.S. Pat. No. 6,576,636 B2 and WO 01/18013 or particular formulations such as liposomes (U.S. Pat. No. 5,223,263) designed for tumour targeting.

Previously, some of the inventors of the present invention have demonstrated that for nucleoside analogues with a conserved β-D configuration of the monosaccharide ring, or for nucleoside analogues with a non-cyclic side chain, the antiviral or anticancer activity can be most efficiently improved through the formation of lipid derivatives of mono-unsaturated ω-9 C18 and C20 fatty acids (Antimicrobial Agents and Chemotherapy, January 1999, p. 53-61, Cancer Research 59, 2944-2949, Jun. 15, 1999, Gene Therapy (1998) 5, 419-426, Antiviral Research 45 (2000) 157-167, Biochemical Pharmacology 67 (2004) 503-511). Not only being more active than the poly-unsaturated counterparts, the preferred mono-unsaturated derivatives are more crystalline and chemically stabile towards oxidation of the lipid chain, hence being more favourable compounds from a chemical and pharmaceutical manufacturing point of view. The Applicant of the present invention has also demonstrated that the mono-unsaturated ω-9 C18 and C20 fatty acids are suited for improvement of the therapeutic activity of a large number of non-nucleoside biologically active compounds (EP 0977725 B1).

A relatively new subgroup of nucleoside analogues are the so called 1,3-dioxolane derivatives. In this class of compounds, the five-membered ring, analogues to the monosaccharide found in natural nucleosides, is conserved, but the $CH_2$ group in position 3 is exchanged with an O atom as shown in formula B below.

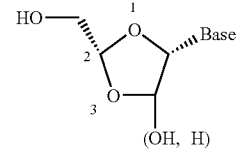

Formula B

Several products within the 1,3-dioxolane class have shown promising antiviral and anti cancer activity in-vitro and in-vivo. For selected compounds, both enhanced, non-nucleoside transporter dependent, cellular uptake and reduced deamination (=inactivation) rate has been shown.

Several types of lipophilic derivatives, including both poly-unsaturated and mono-unsaturated ω-9 C18 and C20 fatty acid ester and amides, of such 1,3,-dioxolane products are known (U.S. Pat. No. 5,817,667, US 2001/0020026 A1 and US 2003/0013660 A1). These references provide both a general teaching about the possible advantages obtained by making such lipid derivatives and the specific benefit of the same regarding activity in disease and mechanistic models. In particular, the in-vitro anti cancer activity of the $N^4$-amide derivatives of (−)-β-L-dioxolane-cytidine (troxacitabine) made with the following fatty acids, oleic acid (cis-9-octadecenoic acid), elaidic acid (trans-9-octadecenoic acid) and linoleic acid (cis-9,12-octadecadienoic acid), have been compared in several cell lines. The three products have quite comparable activity, the oleic acid amid derivative being marginally better (2 to 5 times) than the elaidic counterpart.

DESCRIPTION OF THE INVENTION

There has now surprisingly been found that the activity of 1,3-dioxolane nucleoside derivatives can be significantly enhanced as compared to the prior art compounds through the formation of derivatives of certain unsaturated long chain fatty acids with at least one double bond in position 6 counted from the carbonyl carbon atom, commonly recognised as $\Delta^6$ unsaturated fatty acid. Both ester and amide derivatives of mono- and poly-$\Delta^6$-unsaturated fatty acid derivatives of 1,3-dioxolane nucleoside analogues have been examined, and are herein demonstrated with, and compared to the prior art compounds of the particular product troxacitabine. In detail, the ester and amide derivatives of petroselinic acid (cis-6-octadecenoic acid), petroselaidic acid (trans-6-octadecenoic acid), gamma-linolenic acid (cis-6,9,12-octadecatrienoic acid) and elaidic acid amide have been tested as a prior art comparator compound. The petroselaidic acid derivatives are the most potent. They are equally active, marginally better than the gamma-linolenic acid derivative, and 20 fold more active than the prior art product, troxacitabine-$N^4$-elaidic acid amide.

In a separate experiment, the in-vitro activity of the amide derivative of petroselinic acid was compared to the prior art product troxacitabine-$N^4$-elaidic acid amide in the breast tumour line MaTu and its adriamycin resistant subline MaTu/Adr. Surprisingly, there has been found that the good activity of the troxacitabine-petroselinic amide in the MaTu line was unchanged in the MaTu/Adr sub line while for the troxacitabine-$N^4$-elaidic acid amide, a resistance factor of 6 was observed.

The compounds of this invention can be characterized by the general formula I:

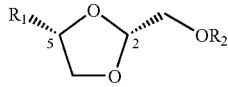

(I)

wherein the substituents in position 2 and 5 of the 1,3 dioxolane ring has the possibility to be above or below the plane of the five-membered ring. The said substituents can be in either a cis or a trans configuration. $R_2$ represents a hydrogen atom or a unsaturated fatty acid acyl group $R_5C(O)$, $R_5CH_2OC(O)$ or $R_5CH_2NHC(O)$ where $R_5$ is a $C_{7-23}$ alkenyl residue of the general formula

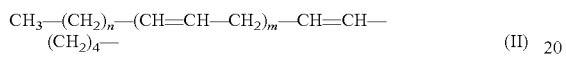

(II)

wherein m is a number from 0 to 2 and n is a number from 0 to 10.

$R_1$ denotes an optionally substituted nitrogen base possibly carrying a functional group such as an alcohol or an amino group, such group optionally being acylated with an unsaturated fatty acid.

More specifically, $R_1$ is

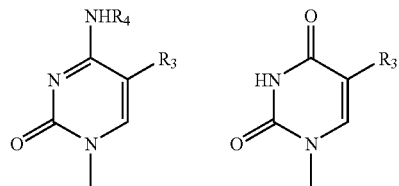

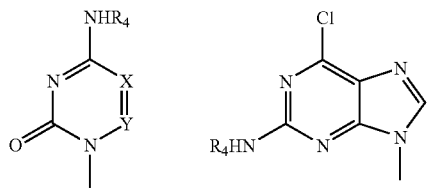

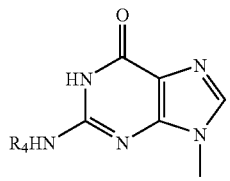

and $R_3$ is selected from the group consisting of hydrogen, methyl, trifluoromethyl, fluorine, chlorine, bromine or iodine; and Z and W are each independently Br, Cl, I, F, $OR_4$ or $NHR_4$ and at least one of Z and W is either $OR_4$ or $NHR_4$, and $R_4$ is H or $R_5C(O)$, $R_5CH_2OC(O)$ or $R_5CH_2NHC(O)$ where $R_5$ is a $C_{7-23}$ alkenyl of the general formula II. $R_2$, $R_3$ and $R_4$ cannot simultaneously be hydrogen. X and Y can be either CH or a N atom with at least one of X or Y being N.

It is noted that the $\Delta^6$ unsaturated fatty acids contemplated in this invention can have both cis and trans stereochemistry of the double bonds.

Particularly preferred embodiments of this invention is exemplified with, but not limited to, troxacitabine-2'-hydroxymethyl-trans-6-octadecenoic acid ester, troxacitabine-$N^4$-trans 6-octadecenoic acid amide, troxacitabine-2'-hydroxymethyl-gamma-linolenoic acid ester and troxacitabine-$N^4$-cis 6-octadecenoicacid amide.

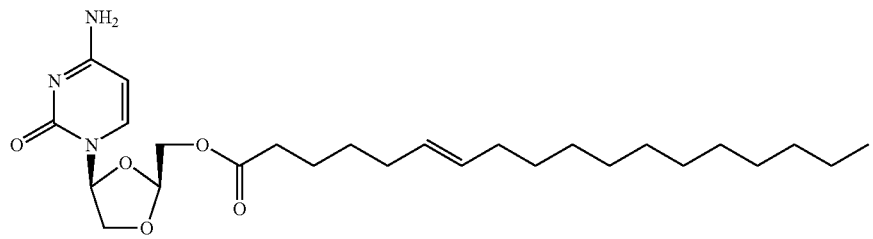

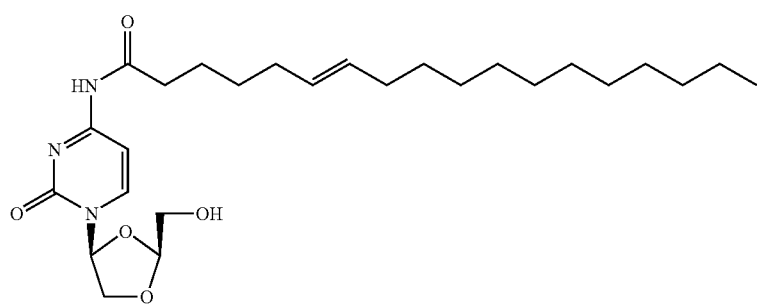

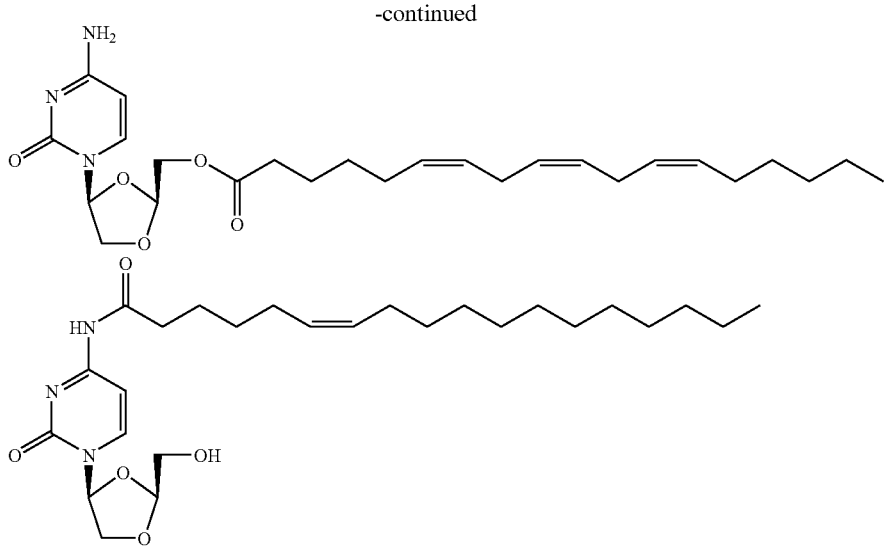

EXAMPLE 1

The cervical cancer cell line HeLa/mut was seeded, $5 \times 10^3$ cells per well, in 96-well-plates. The medium was RMPI 1640 with 2 mM Glutamine and 10% Foetal Bovine Serum. 24 hours later the test compounds were added in 6 concentrations. The cells were incubated for 4 days. The MTT solution was added to each well and incubated for 4 hours. The samples were read by an ELISA reader at 540 nm. The IC50 values were determined from growth curves. The test compounds were troxacitabine elaidic amid, troxacitabine petroselaidoate, troxacitabine-petroselaidic amide and troxacitabine γ-linolenoate. Surprisingly the activity of troxacitabine petroselaidoate and petroselaidic amide was 20 fold more active than troxacitabine elaidic amid.

| Compound | IC50 μM ± Standard Deviation |
| --- | --- |
| troxacitabine elaidic-amide | 3.58 ± 2.56 |
| troxacitabine petroselaidoate | 0.18 ± 0.12 |
| troxacitabine-petroselaidic amide | 0.15 ± 0.07 |
| troxacitabine γ-linolenoate | 0.83 ± 0.59 |

EXAMPLE 2

The human cervical cancer cell line HeLa/mut and the adriamycin resistant cell line HeLa/mut/Adr were seeded, $5 \times 10^3$ cells per well, in 96-well-plates. The medium was RMPI 1640 with 2 mM Glutamine and 10% Foetal Bovine Serum. 24 hours later the test compounds were added in a final volume of 20 μl to the cells, in six different concentrations. The cells were incubated for 4 days. MTT solution was added to each well and incubated for 4 hours. The samples were read by an ELISA reader at 540 nm. The IC50 values were determined from growth curves. The resistance factor is the IC50 in HeLa/mut/Adr vs. IC50 in HeLa/mut. The test compounds were troxacitabine-elaidic amide and troxacitabine-petroselinic amide. Surprisingly we found the troxacitabine-petroselinic amide to be independent of the adriamycin resistance, with a resistance factor of 1.0, compared to 5.8 for troxacitabine-elaidic amide.

| Compound | Resistance factor = (IC50 HeLa/mut/Adr)/(IC50 HeLa/mut) |
| --- | --- |
| troxacitabine-elaidic amide | 5.8 |
| troxacitabine-petroselinic amide | 1.0 |

EXAMPLE 3

The U937 and THP-1 cell lines were seeded, 20 000 cells per well, in 96-well-plates. 50 μl medium ( ) was added to each well. At the same time test compounds were added in 5 different concentrations and incubated for 48 hours. The Cell-Titer 96® Non-Radioactive cell proliferation assay (Promega) was used to study the cytotoxicity of test in these cells. This assay is a colorimetric method for determining the number of viable cells in proliferation or chemosensitivity assays. It is composed of solutions of a novel tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS). MTS is bioreduced by cells into a formazan product that is soluble in tissue culture medium. The absorbance of the formazan at 490 nm can be measured directly from 96 well assay plates without additional processing. The quantity of formazan product as measured by the amount of 490 nm absorbance is directly proportional to the number of living cells in culture (IC50 values). The test compounds were troxacitabine-5'-elaidic acid ester, α-troxacitabine N4-elaidic acid amide, troxacitabine-5'-petroselaidoate, troxacitabine-5'-oleate, troxacitabine N4-petroselaidic acid amide, troxacitabine C5'-6,9,12-linolenoate, troxacitabine N4-6,9,12-linolenic acid amide, troxacitabine-5'-petroselinoate and troxacitabine N4-petroselinic acid amide. In both cell lines, all compounds resulted in a severe cytotoxicity of the cells and troxacitabine-5'-petroselinoate, troxacitabine N4-6,9,12-linolenic acid amide, troxacitabine N4-petroselinic acid amide were even more active than the other compounds, which also resulted in high activity, except for α-troxacitabine N4-elaidic acid amide as expected.

| Compound | U937 cells IC50 μM ± SD | THP-1 cells IC50 μM ± SD |
|---|---|---|
| Troxacitabine-5'-elaidic acid ester | 0.06 μM ± 0.01 | 0.06 μM ± 0.01 |
| α-troxacitabine N4-elaidic acid amide | 10 μM ± 0.4 | nd |
| Troxacitabine-5'-petroselaidoate | 0.08 μM ± 0.02 | 0.06 μM ± 0.01 |
| Troxacitabine-5'-oleate | 0.09 μM ± 0.02 | 0.07 μM ± 0.02 |
| Troxacitabine N4-petroselaidic acid amide | 0.02 μM ± 0.002 | 0.08 μM ± 0.015 |
| Troxacitabine C5'-6,9,12-linolenoate | 0.09 μM ± 0.008 | 0.16 μM ± 0.03 |
| Troxacitabine N4-6,9,12-linolenic acid amide | 0.007 μM ± 0.001 | 0.085 μM ± 0.03 |
| Troxacitabine-5'-petroselinoate | 0.007 μM ± 0.001 | 0.09 μM ± 0.01 |
| Troxacitabine N4-petroselinic acid amide | 0.009 μM ± 0.001 | 0.06 μM ± 0.01 |

SD = Standard deviation
nd = not done

EXAMPLE 4

Troxacitabine $N^4$-Elaidic Acid Amide (Comparative compound)

Troxacitabine (150 mg, 0.70 mmol), TEA (0.1 ml, 0.74 mmol) and DMAP (90 mg, 0.74 mmol) in dry DCM/DMF (5 ml/2 ml) was added elaidoyl chloride in DCM (5 ml). The acid chloride was prepared from elaidic acid (209 mg, 0.74 mmol), oxalyl chloride (0.4 ml, 2.96 mmol) and DMF (catalytic amount) in toluene (10 ml) by stirring at ambient temperature for 2 h and then evaporated to dryness. After stirring for 22 h at room temperature a saturated aqueous solution of $NH_4Cl$ was added and the phases separated. The aqueous phase was extracted with DCM (3×), and the combined organic extracts were washed with saturated brine, dried ($Na_2SO_4$), filtered and evaporated in vacuuo. The product was purified by flash chromatography on silica gel eluting with MeOH/DCM (25:975) followed by MeOH/DCM (5:95) to give 208 mg (62%) of the desired product as colourless crystals.

$^1$H-NMR (200 MHz; $CDCl_3$); δ 8.51 (1H, d), 7.43 (1H, d), 6.21 (1H, m), 5.39 (2H, m), 5.18 (m, 1H), 4.40-4.12 (m, 2H), 4.01 (m, 2H), 2.44 (t, 2H), 2.2-1.9 (m, 6H), 1.8-1.1 (m, 22H), 0.96 (t, 3H).

MS (electrospray); 500 $[M+Na]^+$.
HPLC: 99.4%

EXAMPLE 5

Troxacitabine-2'-hydroxymethyl-petroselaidoate

Troxacitabine (0.5 g, 2.4 mmol) in dry DMF (10 ml) was added a solution of HCl in DMF (1.3 M, 2.2 ml, 2.8 mmol), which had been prepared by bubbling HCl-gas through DMF. After some seconds a colourless solid precipitated from the solution. The resulting mixture was stirred for 30 min. and petroselaidoyl chloride in DMF (5 ml) was then added. The acid chloride had previously been prepared from petroselaidic acid (1.0 g, 3.5 mmol), oxalyl chloride (1.9 ml, 14 mmol) and DMF (catalytic amount) in DCM (30 ml) by stirring at ambient temperature for 1 h and then evaporated to dryness. After stirring for 64 h at room temperature the mixture was poured into water and extracted with DCM (3×). The combined organic extracts were washed with a saturated aqueous solution of $NaHCO_3$, brine, dried ($Na_2SO_4$), filtrated and evaporated in vacuuo. The product was purified by flash chromatography on silica gel eluting with MeOH/DCM (5:95) to give 0.52 g (46%) of the desired product as colourless crystals.

$^1$H-NMR (200 MHz; $CDCl_3$); δ 7.74 (d, 1H), 6.27 (m, 1H), 5.87 (d, 1H), 5.40 (m, 2H), 5.22 (m, 1H), 4.6-4.2 (m, 4H), 2.42 (t, 2H), 2.00 (m, 4H), 1.65 (m, 2H), 1.5-1.2 (m, 22H), 0.87 (t, 3H).

MS (electrospray); 478 $[M+H]^+$, 500 $[M+Na]^+$.
HPLC; 93.7%

EXAMPLE 6

Troxacitabine $N^4$-petroselaidic acid amide

Petroselaidic acid (662 mg, 2.35 mmol) in DCM (20 ml) was added TEA (0.33 ml, 2.35 mmol) followed by TBTU (753 mg, 2.35 mmol), and stirred for 40 min. at RT before troxacitabine (0.5 g, 2.35 mmol) in DMF (2 ml) was added. After stirring for 22 h at RT a saturated aqueous solution of $NH_4Cl$ was added and the phases separated. The aqueous phase was extracted with DCM (3×), and the combined organic extracts were washed with saturated $NaHCO_3$, brine, dried ($Na_2SO_4$), filtered and evaporated in vacuuo. The product was purified by flash chromatography on silica gel eluting with MeOH/DCM (25:975) to give 650 mg (58%) of the desired product as colourless crystals.

$^1$H-NMR (200 MHz; $CDCl_3$); δ 8.57 (d, 1H), 7.47 (d, 1H), 6.21 (d, 1H), 5.42 (m, 2H), 5.16 (s, 1H), 4.4-4.2 (m, 2H), 4.01 (m, 2H), 2.49 (t, 2H), 2.02 (m, 4H), 1.71 (m, 2H), 1.5-1.2 (m, 22H), 0.87 (t, 3H).

MS (electrospray); 478 $[M+H]^+$, 500 $[M+Na]^+$.
HPLC; 93.8%

EXAMPLE 7

Troxacitabine 2'-hydroxymethyl-6,9,12-linolenoate

Troxacitabine (0.7 g, 3.3 mmol) in dry DMF (17 ml) was added a solution of HCl in DMF (1.3 M, 3.0 ml, 3.9 mmol), which had been prepared by bubbling HCl-gas through DMF. After some seconds a colourless solid precipitated from the solution. The resulting mixture was stirred for 30 min. before acid chloride in DMF (4 ml) was added. The acid chloride had previously been prepared from GLA (2.19 g, 7.9 mmol), oxalyl chloride (2.66 ml, 31.4 mmol) and DMF (catalytic amount) in DCM (50 ml) by stirring at ambient temperature for 3 h and then evaporated to dryness. After stirring for 48 h at room temperature the mixture was poured into aqueous NaHCO$_3$ and extracted with DCM (3×). The combined organic extracts were washed with brine, dried (Na$_2$SO$_4$), filtered and evaporated in vacuuo. The product was purified by flash chromatography on silica gel eluting with MeOH/DCM (3:100) to give 0.85 g (54%) of the desired product as a pale yellow solid.

$^1$H-NMR (200 MHz, CDCl$_3$); δ 7.78 (d, 1H), 6.30 (m, 1H), 6.85 (d, 1H), 5.6-5.1 (m, 7H), 4.6-4.1 (m, 5H), 2.9-2.7 (m, 4H), 2.4 (t, 2H), 2.2-2.0 (m, 3H), 1.8-1.2 (m, 10H), 0.95 (t, 3H).

MS (electrospray); 496 [M+Na$^+$].

HPLC; 93.9%

EXAMPLE 8

Troxacitabine N$^4$-petroselinic acid amide

Petroselinic acid (666 mg, 2.36 mmol) in DCM (20 ml) was added TEA (0.33 ml, 2.37 mmol) followed by TBTU (753 mg, 2.35 mmol), and stirred for 40 min. at RT before troxacitabine (0.501 g, 2.35 mmol) in DMF (2 ml) was added. After stirring for 22 h at RT a saturated aqueous solution of NH$_4$Cl (25 mL) was added and the phases separated. The aqueous phase was extracted with DCM (3×50 mL), and the combined organic extracts were washed with saturated NaHCO$_3$ (25 mL), brine (25 mL), dried (Na$_2$SO$_4$), filtered and evaporated in vacuuo. The product was purified by flash chromatography on silica gel eluting with MeOH/DCM (25:975-50:950) to give 599 mg (53%) of the desired product as colourless crystals.

$^1$H-NMR (200 MHz; CDCl$_3$); δ 8.48 (bs, 1H), 8.42 (d, J=7.4 Hz, 1H), 7.39 (d, J=7.5 Hz, 1H), 6.16 (d, J=4.7 Hz, 1H), 5.31 (m, 2H), 5.09 (s, 1H), 4.18-4.33 (m, 2H), 3.94 (d, J=4.8 Hz, 2H), 2.40 (t, J=7.3 Hz, 2H), 2.02 (m, 4H), 1.63 (m, 2H), 1.23-1.44 (m, 21H), 0.84 (t, J=6.0 Hz, 3H).

MS (electrospray, pos.); 500 [M+Na]$^+$.

MS (electrospray, neg.); 477 [M+]$^+$.

HPLC; 93%

EXAMPLE 9

Troxacitabine-2'-hydroxymethyl-petroselinoate

Troxacitabine (0.503 g, 2.36 mmol) in dry DMF (7 mL) was added a solution of HCl in DMF (1.3 M, 2.2 ml, 2.86 mmol), which had been prepared by bubbling HCl-gas through DMF. After some seconds a colourless solid precipitated from the solution. The resulting mixture was stirred for 30 min. and petroselinic acid chloride in DMF (12 mL) was then added. The acid chloride had previously been prepared from petroselinic acid (1.59 g, 5.6 mmol), oxalyl chloride (4.5 mL, 53 mmol) and DMF (0.1 mL catalytic amount) in toluene (35 mL) by stirring at ambient temperature for 2 h and then evaporated to dryness. After stirring for 43 h at room temperature the mixture was poured into water (50 mL) and extracted with DCM (3×100 mL) The combined organic extracts were washed with a saturated aqueous solution of NaHCO$_3$ (50 mL), brine (50 mL), dried (Na$_2$SO$_4$), filtrated and evaporated in vacuuo. The product was purified by flash chromatography on silica gel eluting with MeOH/DCM (25:975-50:950) to give 0.686 g (61%) of the desired product as pale yellow crystals.

$^1$H-NMR (200 MHz; CDCl$_3$); δ 7.69 (d, J=7.4 Hz, 1H), 6.21 (m, 1H), 5.70 (d, J=7.4 Hz, 1H), 5.30 (m, 2H), 5.16 (m, 1H), 4.45 (dd, J=3.4 Hz, 12.3 Hz, 1H), 4.16-4.28 (m, 3H), 2.34 (t, J=7.4 Hz, 2H), 1.99 (m, 4H), 1.68 (m, 2H), 1.22-1.38 (m, 22H), 0.84 (t, J=6.4 Hz, 3H).

MS (electrospray, posy; 500 [M+Na]$^+$.

MS (electrospray, neg); 477 [M+]$^+$.

HPLC; 94%

EXAMPLE 10

Troxacitabine N$^4$-6,9,12-linolenic acid amide

Gamma linolenic acid (GLA) (0.38 g, 1.8 mmol) dissolved in DCM (4 ml) was added TEA (245 uL, 1.8 mmol) and TBTU (0.57 g, 1.8 mmol). The solution was allowed to stir for 30 min. at RT before troxacitabine (0.38 g, 1.8 mmol) in DCM (2 ml) was added. The reaction mixture was stirred for 70 h at RT before a saturated aqueous solution of NH$_4$Cl was added and the mixture extracted with DCM (3×). The combined organic phases were washed with brine, dried (NaSO$_4$), filtered and evaporated in vacuuo. The desired product was isolated by flash chromatography on silica gel eluting with MeOH/DCM (3:200) to give 0.30 g (35%) of the title compound as a pale yellow solid.

$^1$H-NMR (200 MHz, CDCl$_3$); δ 8.5 (d, 1H), 7.45 (d, 1H), 6.20 (d, 1H), 6.6-6.3 (m, 6H), 5.15 (s, 1H), 4.3 (m, 2H), 4.0 (s, 2H), 2.8 (m, 5H), 3.5 (m, 3H), 2.1 (m, 4H), 1.7 (m, 2H), 1.4 (m, 6H), 0.95 (m, 3H).

MS (electrospray); 496 [M+Na$^+$].

HPLC; 97.0%

| HPLC-parameters: | |
|---|---|
| HPLC-system: | Agilent 1100 |
| Column: | Cromolith Speedrod RP-C18e 50 × 4.6 mm |
| Time of analysis: | 15 min |
| Flow: | 2 ml/min |
| Mobil phase: | A: 5% MeOH in water added phosphate-buffer (pH = 6) |
| B: | MeOH added phosphate-buffer (pH = 6) |
| Temperature: | 40° C. |
| Detector: | UV 240-300 nm |

The invention claimed is:
1. A compound having the following formula (I):

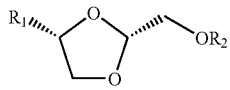  (I)

wherein:
R$_1$ is

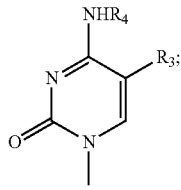

R$_4$ is H or R$_5$C(O), R$_5$CH$_2$OC(O) or R$_5$CH$_2$NHC(O) where R$_5$ is a C$_{7-23}$ alkenyl of the general formula

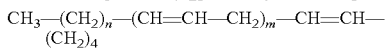  (II)

wherein m is a number from 0 to 2 and n is a number from 0 to 10; and
R$_2$ is H or R$_5$C(O), R$_5$CH$_2$OC(O) or R$_5$CH$_2$NHC(O) where R$_5$ is a C$_{7-23}$ alkenyl of the general formula

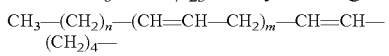  (II)

wherein m is a number from 0 to 2 and n is a number from 0 to 10, with the proviso that R$_2$ and R$_4$ cannot simultaneously be hydrogen, or a pharmaceutically acceptable salt thereof.

2. The compound according to claim 1 defined as:

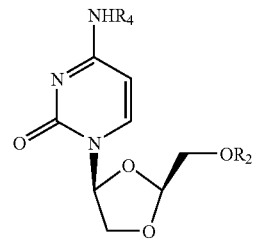

wherein R$_2$ is H or R$_5$C(O), R$_5$CH$_2$OC(O) or R$_5$CH$_2$NHC(O) and R$_4$ is H or R$_5$C(O), R$_5$CH$_2$OC(O) or R$_5$CH$_2$NHC(O) where R$_5$ is a C$_{7-23}$ alkenyl of the general formula

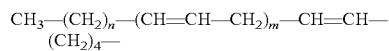  (II)

wherein m is a number from 0 to 2 and n is a number from 0 to 10, with the proviso that R$_2$ and R$_4$ cannot simultaneously be hydrogen, or a pharmaceutically acceptable salt thereof.

3. The compound according to claim 1 selected from the group consisting of:

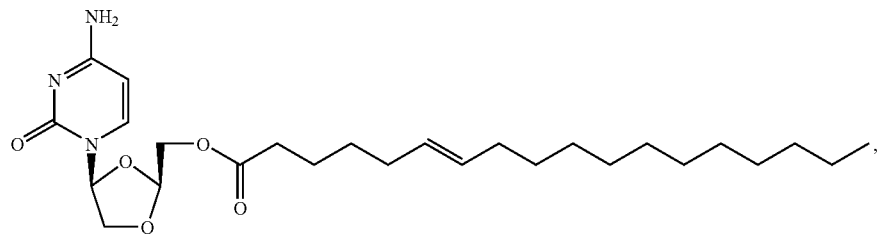

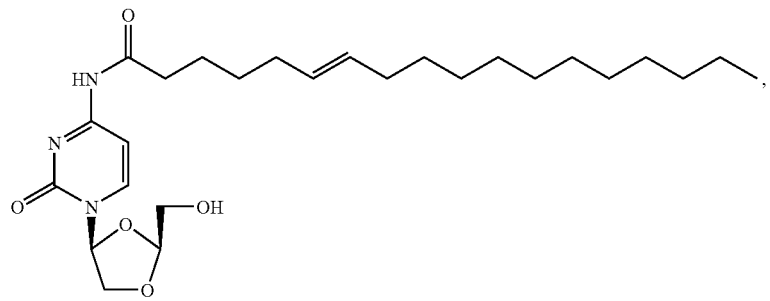

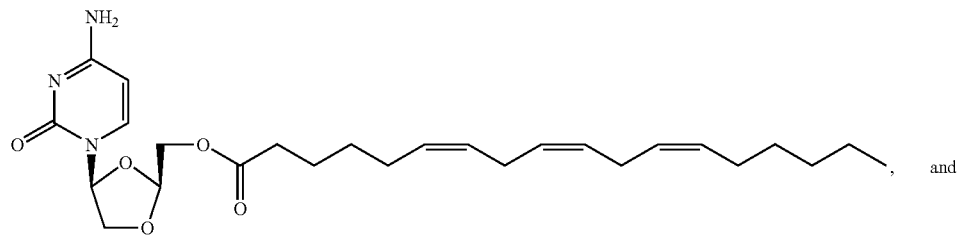, and

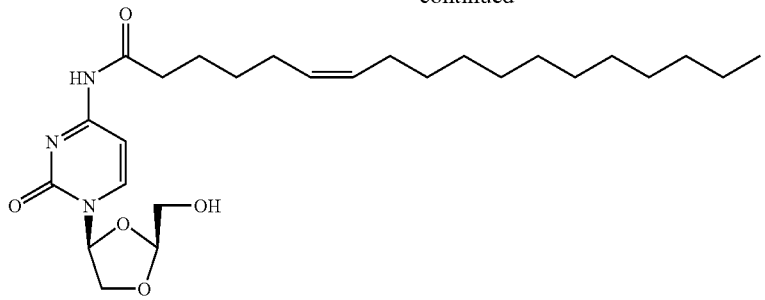

or a pharmaceutically acceptable salt thereof.

4. A method for treating cancer in a subject in need of such treatment, which comprises administering to such subject a therapeutically effective amount of a compound of formula (I) as defined in claim 1 or a pharmaceutically acceptable salt thereof,
   wherein the cancer is selected from the group consisting of cervical cancer and leukemias.

5. A pharmaceutical composition, comprising a compound of formula (I) as defined in claim 1, and a pharmaceutically acceptable excipient, diluent and/or carrier therefor.

6. The method for treating cancer according to claim 5, wherein the cancer is a solid tumor.

7. The method for treating cancer according to claim 5, wherein the cancer is a leukemia.

* * * * *